United States Patent [19]

Hokanson et al.

[11] Patent Number: 5,103,825
[45] Date of Patent: Apr. 14, 1992

[54] DOPPLER TRANSDUCER PROBE WITH DIRECTION INDICATOR

[75] Inventors: D. Eugene Hokanson, Mercer Island; Roger C. Nelson, Issaquah, both of Wash.

[73] Assignee: D. E. Hokanson, Inc., Bellevue, Wash.

[21] Appl. No.: 664,693

[22] Filed: Mar. 5, 1991

[51] Int. Cl.⁵ ............................................. A61B 8/02
[52] U.S. Cl. ........................... 128/661.07; 128/661.08; 128/662.03; 128/662.04
[58] Field of Search ...................... 128/661.07, 661.08, 128/661.09, 662.03, 662.04, 660.10

[56] References Cited

U.S. PATENT DOCUMENTS

| | | | |
|---|---|---|---|
| 3,964,296 | 6/1976 | Matzuk | 128/660.10 |
| 4,515,164 | 5/1985 | Slavin | 128/661.08 |
| 4,986,276 | 1/1991 | Wright | 128/662.01 |
| 4,995,396 | 2/1991 | Inaba et al. | 128/662.03 |

OTHER PUBLICATIONS

"Letters to the Editor," Ultrasound in Med. & Biol, vol. 2, (Feb. 1976) p. 135.
A Pilot Clinical PEP Monitor, Transactions on Biomedical Engineering, vol. BME-26, No. 6, Jun. 1979, pp. 345-349.
The Complete Doppler CW-1A Sheet of D. E. Hokanson, Inc., published at least as early as 1985.

Primary Examiner—Francis Jaworski
Assistant Examiner—George Manuel
Attorney, Agent, or Firm—Christensen, O'Connor, Johnson & Kindness

[57] ABSTRACT

Current-responsive light-emitting diodes of different colors are provided adjacent to the tip of the hand-held transducer probe of a medical Doppler device. Mechanism is provided to actuate the diodes of one color when the direction of internal body matter detected by the Doppler device is toward the probe and to actuate lights of a different color when the direction of detected internal body matter is away from the probe. In addition, power supply to the diodes is controlled so that increasing brightness indicates increasing velocity of the detected internal body matter.

10 Claims, 2 Drawing Sheets

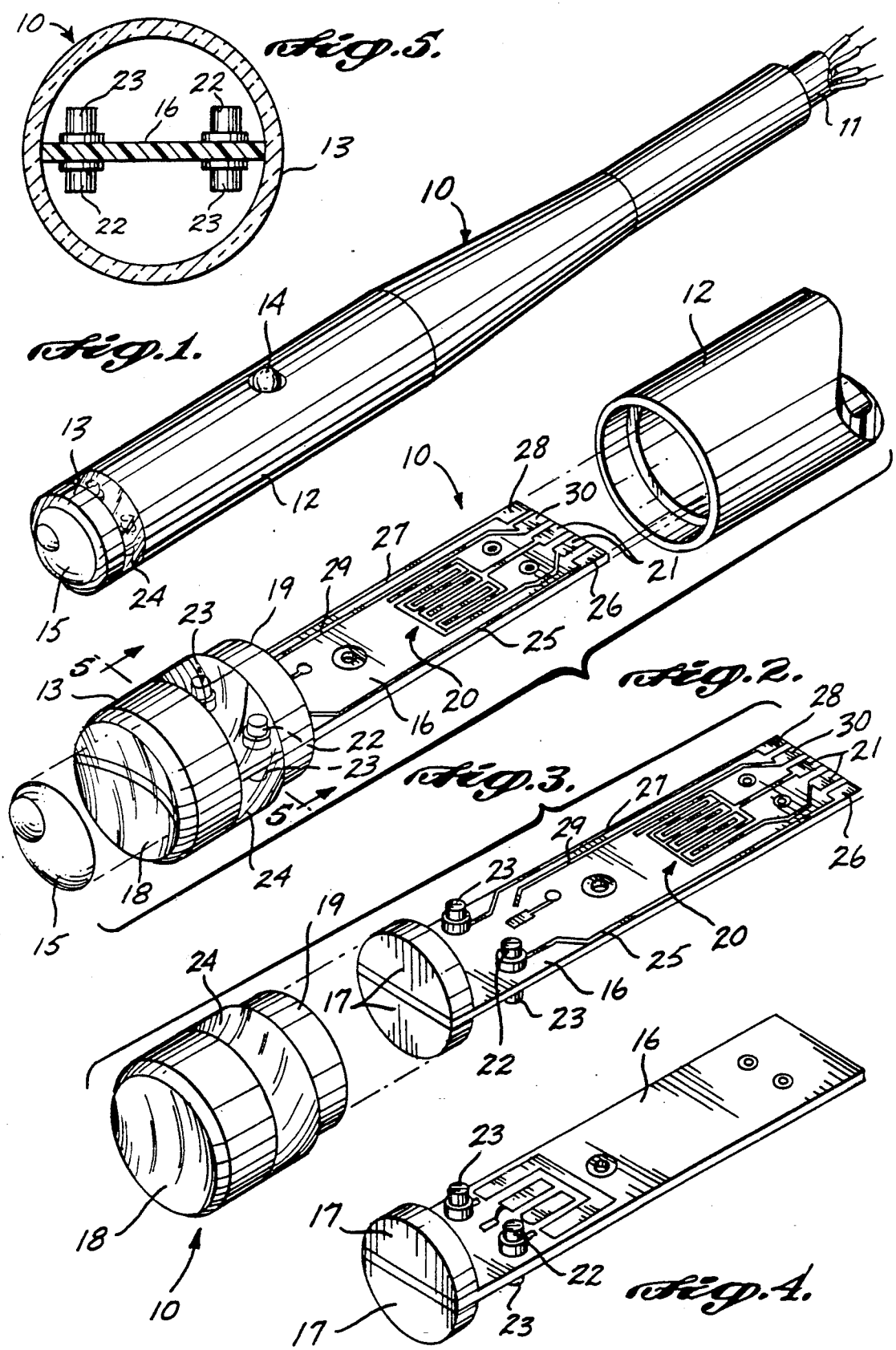

DOPPLER TRANSDUCER PROBE WITH DIRECTION INDICATOR

BACKGROUND OF THE INVENTION

1. Field of the Invention

The present invention relates to a hand-held transducer probe of a medical Doppler device. More specifically, the present invention relates to a probe which has mechanism for visually indicating the relative direction of internal body matter reflecting ultrasound waves transmitted from the probe. Such mechanism indicates whether the reflecting matter is moving toward or away from the probe.

2. Prior Art

In a continuous wave medical Doppler ultrasound device, a transmitting transducer beams ultrasound waves of a known frequency into the body. A receiving transducer is positioned closely adjacent to the transmitting transducer. For example, both the transmitting transducer and receiving transducer can be incorporated in a slender "probe" connected to the remainder of the medical Doppler ultrasound device by an electrical cable. The receiving transducer detects waves reflected from internal body matter such as blood. In accordance with the well-known Doppler effect, the difference in frequency of a wave before and after reflection indicates the velocity of the reflecting matter relative to the wave transmitter.

In pulsed medical Doppler devices, a single transducer can be used to transmit bursts of ultrasound waves spaced in time and, between transmissions, the same transducer is used to detect reflected waves.

Conventional medical Doppler devices generate electrical signals based on the frequency difference between transmitted and reflected waves. Such signals often are in the audible frequency range. Consequently, one convenient output is simply an audible output having a frequency content identical to the frequency content of the electrical signal. The electrical signal can be amplified and used to drive speakers or headphones. When a probe is pointed at an angle toward an artery, the audible output sounds like pulsed swishing of blood through the artery caused by beating of the heart.

Known devices provide various other types of outputs such as chart records of amplitude and/or frequency content or real time frequency spectrum graphs on a video display.

A single electrical signal corresponding to the frequency difference between transmitted and reflected waves provides an accurate indication of relative speed when the angle of transmitted and reflected waves relative to the direction of movement of the reflecting internal body matter is known. A single signal does not provide an indication of the relative direction, i.e., whether the reflecting matter is moving toward or away from the probe. It is known, however, that direction can be detected by providing quadrature outputs which are outputs that are identical but differ in phase by 90 degrees. Either signal provides velocity information and direction is indicated by which of the two outputs is leading in phase.

In a blood flowmeter, speed may be indicated by the frequency of an audible output and/or a visual display on the master control unit, volume of blood flow may be indicated by audible volume and/or visual information on the master unit, and direction may be indicated by stereo headphone or speaker channels and/or by visual indicators on the master unit. It may be difficult for a user to keep track of the desired information while at the same time manipulating the probe and then maintaining it at a desired location and angle.

SUMMARY OF THE INVENTION

The principal object of the present invention is to provide mechanism for conveniently indicating to the user of a medical Doppler ultrasound device at least the direction and preferably both the direction and approximate velocity of internal body matter relative to a transducer probe in a form which simplifies use of the device.

In a preferred embodiment of the present invention, the foregoing object is accomplished by providing easily distinguishable visual indicators incorporated in the probe itself, preferably close to the tip, which immediately inform the user of the relative direction of internal body matter reflecting the transmitted ultrasound waves. Such visual indicators can be current responsive light-emitting diodes. The diodes can be actuated so that a plurality of diodes of one color indicate flow toward the transducer probe and a plurality of diodes of a different color indicate flow away from the probe. The diodes can be arranged around the tip portion of the probe so that at least one diode of each color always is visible to the user. The diodes can be controlled such that increasing brightness corresponds to increasing velocity of the internal body matter being scanned.

BRIEF DESCRIPTION OF THE DRAWINGS

FIG. 1 is a top perspective of the probe of a medical Doppler ultrasound device having a direction indicator in accordance with the present invention.

FIG. 2 is an enlarged fragmentary top perspective of the probe of FIG. 1 with some parts shown in exploded relationship.

FIG. 3 is a top perspective of components of the probe of FIGS. 1 and 2 shown in further exploded relationship; and FIG. 4 is a perspective of the underside of one of such components.

FIG. 5 is a transverse section along line 5—5 of FIG. 2.

DETAILED DESCRIPTION

Figure 6:
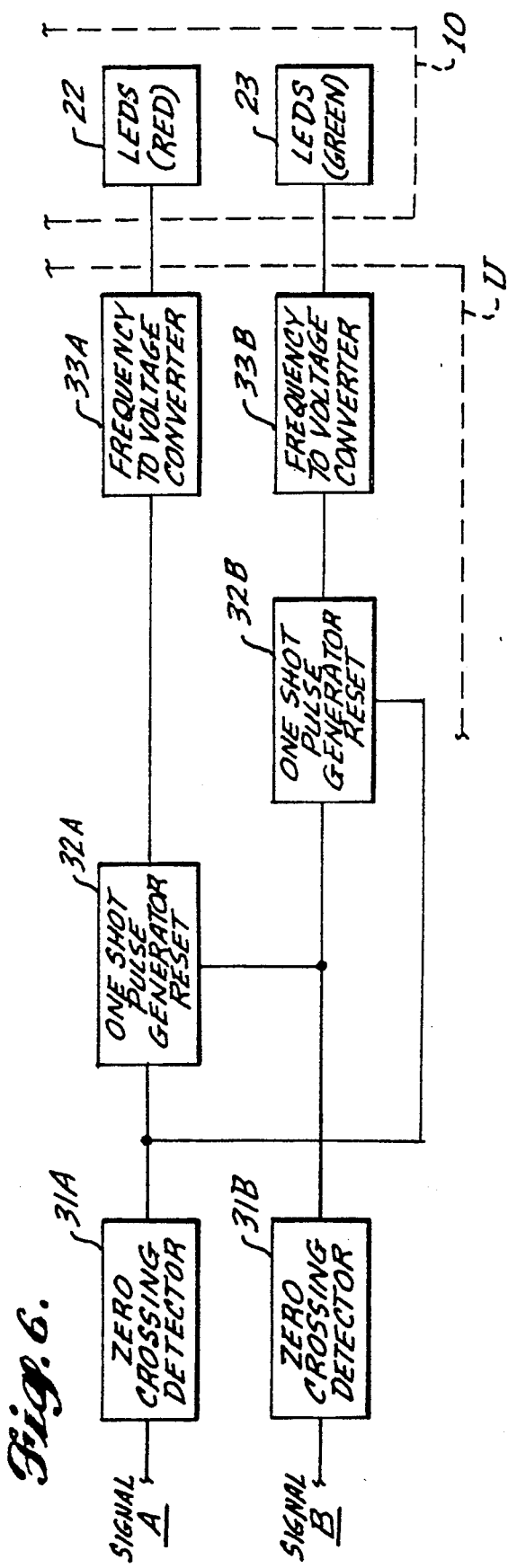
FIG. 6 is a block diagram of circuit components of the present invention.

In accordance with the present invention, a direction indicator is incorporated in a hand-held probe of a medical Doppler device. Probe 10 shown in FIG. 1 is long and slender and is intended to be held like a pencil. In a representative embodiment, such probe can be about 5 inches (12.70 cm) long and have a maximum diameter of about ½ inch (1.27 cm). The only connection of the probe 10 to the master control unit (not shown) of a medical Doppler device is by a flexible electrical cable 11.

Probe 10 has a rigid outer body or casing 12 forming a handle and a free end portion in the form of a rigid tip portion 13 remote from the cable 11. An actuating button 14 is provided which, when depressed, results in ultrasound waves being transmitted from the tip approximately axially of the casing 12 through a lens 15. Lens 15 can be of the type shown in U.S. Pat. No. 4,532,933.

The cylindrical casing 12 is hollow, as shown in FIG. 2. In the representative embodiment illustrated, the probe is for use in a continuous wave medical Doppler ultrasound device. As seen in FIGS. 3 and 4, the transmitting and receiving transducers are substantially semi-circular disks 17 having their flat diametral edges secured along the top and bottom end margins of a thin rectangular circuit board 16 of nonconductive material. The generally cylindrical tip portion 13 of the probe is fitted over the transducers and can be secured in position by suitable adhesive or epoxy with the transducers butted against the closed front end 18 of such tip portion. The open rear end portion 19 of tip section 13 is of reduced diameter for snugly fitting in the hollow casing 12 where the tip section can be similarly permanently affixed by adhesive.

Small wires (not shown in FIGS. 2 through 5) from the master control unit extend through the casing 12 and are connected to the transmitting and receiving transducers 17. One pair of wires powers the transmitting transducer. Circuit board 16 has a small array 20 of alternating unconnected conductors positioned to be in alignment with a conductive inner portion of the spring-biased button 14 shown in FIG. 1. Such alternating conductors terminate in larger conductive patches 21 on the end of the circuit board remote from the transducers 17. Patches 21 normally are in an open circuit condition unless the button 14 is depressed, in which case a closed circuit condition is detected by the master control unit and power is conveyed to the transmitting transducer for generating an ultrasound beam through the lens 15.

Another pair of wires (not shown) extends from the receiving transducer to the master control unit to convey electrical signals generated by the receiving transducer. Such signals result from reflected ultrasound waves impinging on the receiving transducer.

In accordance with the present invention, two light-emitting diodes 22 are mounted adjacent to the transducers 17, close to opposite longitudinal edges of circuit board 16 on its opposite flat surfaces, respectively. Each of two differently colored diodes 23 is mounted directly opposite one of the diodes 22. The diodes are visible through a translucent, preferably substantially transparent, section 24 of the probe tip portion 13, as seen in FIG. 2. In the orientation shown in FIG. 2, the top diodes 22 and 23 are clearly visible and the bottom diode 23 is partially visible. Regardless of the rotative orientation of the probe, at least one diode 22 and one diode 23 will be readily visible by the user.

A conductive strip 25 extends from a larger conductive end patch 26 of the circuit board for conveying power to diodes 22. At the other side of the circuit board, a similar strip 27 extends from an end patch 28 for supplying power to diodes 23. Diodes 22 and 23 have a common ground from a strip 29 leading from larger end patch 30. Wires (not shown) can be soldered or otherwise suitably connected to the patches 21, 26, 28 and 30 and extend to the Doppler master control unit through the cable 11.

With reference to FIG. 6, the present invention is used with standard Doppler circuitry of the type providing quadrature output signals labeled A and B in FIG. 6. Such circuitry is housed in the master control unit U to which the transducer probe 10 is connected. Each signal is fed to its own zero crossing detector 31A or 31B of conventional design. The output of each detector is a square wave having a frequency identical to the frequency of its input. In a representative embodiment the square wave can vary in amplitude from 0 to 9 volts, but other voltages can be used depending on the other circuit components.

The output of detector 31A is fed to a conventional one-shot pulse generator 32A and the output of detector 31B is fed to an identical conventional one-shot pulse generator 32B. In addition, the output of detector 31A is fed to a "reset" or "disable" input of generator 32B and the output of detector 31B is fed to a "reset" or "disable" input of detector 32A. For the signal which is leading in phase, the leading edge of each pulse from the zero crossing detector will activate the corresponding pulse generator. For example, if signal A is leading in phase, a pulse from zero crossing detector 31A will activate pulse generator 32A to produce an output pulse. In the representative embodiment, such pulse can have an amplitude of about 9 volts and a duration of about 20 microseconds. Since that signal (signal A in the illustration) is leading in phase, a square wave pulse from the zero crossing detector (31A in the example) also is fed to the reset or disable input of the other pulse generator (32B in the example). The presence of a positive voltage signal at such reset or disable input prevents pulse generator 32B from generating the pulse which otherwise would be generated when the lagging signal from crossing protector 31B is received. Consequently, only the pulse generator activated by the signal leading in phase is operable to produce an output pulse.

Figure 7:
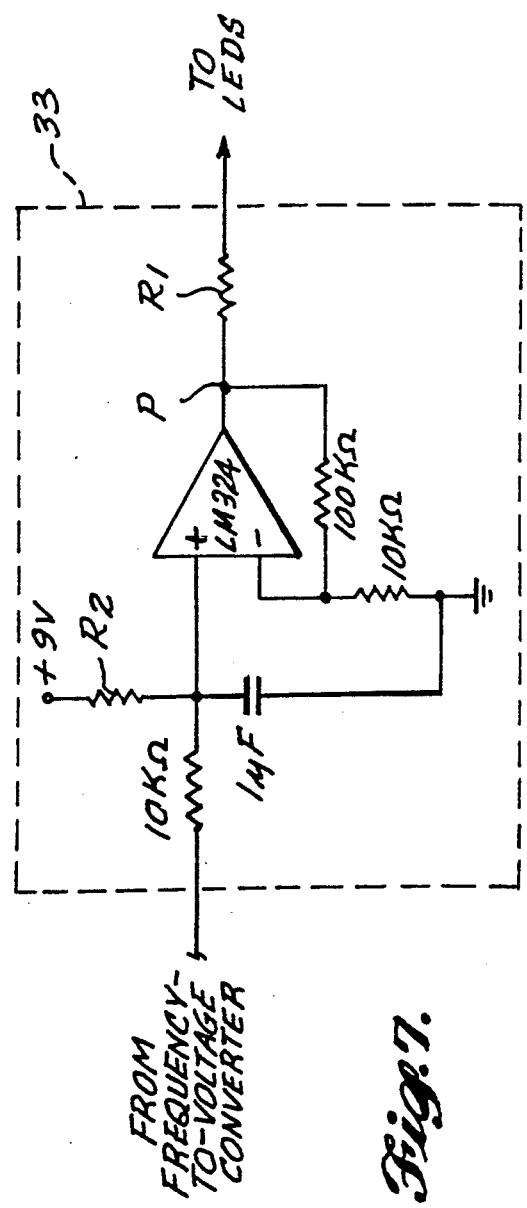
FIG. 7 is a more detailed circuit diagram of one of such components.

In a representative use as a blood flowmeter, the output from the operable pulse generator would be a series of identical pulses (for example, 9 volt amplitude, 20 microsecond duration) having a frequency of 300 hertz to 10 kilohertz which corresponds to the frequency of the triggering quadrature output signal A or B. Such pulse signal is fed to a frequency-to-voltage converter 33A or 33B for which the circuit is shown in FIG. 7. In the illustrated embodiment, the output at point P (in front of the output resistor $R_1$) is a direct current electrical signal of a voltage approximately proportional to the input frequency up to 10,000 kilohertz. Current to the diodes is proportional to voltage and is determined by the values of $R_1$ and $R_2$. Representative values for converter 33A are: $R_1 = 475$ ohms; $R_2 = 34.8$ K ohms. Representative values for converter 33B are: $R_1 = 30.1$ K ohms; $R_2 = 200$ ohms.

Each frequency to voltage converter powers a pair of the light-emitting diodes 22 or 23. As noted above, only one pair is activated at a time depending on which quadrature output signal A or B is leading in phase. In turn, the signal leading in phase indicates the relative direction of the internal body matter reflecting transmitted ultrasound waves. In the preferred embodiment, diodes 22 are red and correspond to signal A leading in phase which is indicative of reflecting matter moving toward the transducers. Diodes 23 are green and are powered when signal B is leading in phase which is indicative of the reflecting matter moving away from the transducers. Since a higher current is provided to the diodes for a higher frequency input, the brightness of the diodes gives a rough approximation of velocity.

The user can position and maintain the probe as desired and receive an immediate visual indication of detected velocity and direction without raising his or her eyes to examine the master control unit and without having to interpret complex video displays.

We claim:

1. In a medical Doppler device for detecting internal body matter and having a control unit and a hand-held transducer probe operably connected to but remote from such unit, the probe being adapted for engagement against the body of a patient, the improvement comprising the combination of a visual indicator located on the probe, and means for actuating said indicator to indicate whether the detected internal body matter is moving toward or away from the probe without adjusting the position of the probe on the body of the patient.

2. In the device defined in claim 1, the probe having a body portion forming a handle and a free end portion adjacent to said body portion, the indicator being located closely adjacent to said free end portion.

3. In a medical Doppler device for detecting internal body matter and having a control unit and a hand-held transducer probe operably connected to but remote from such unit, the improvement comprising the combination of a visual indicator located on the probe, sad indicator including at least one electrically actuated light of a first color and at least one electrically actuated light of a second color different from the first color, and means for actuating said indicator to indicate whether the detected internal body matter is moving forward or away from the probe, said actuating means including means for supplying electric power to the light of the first color when the detected internal body matter is moving toward the probe and for supplying electric power to the light of the second color when the detected internal body matter is moving away from the probe.

4. In the device defined in claim 3, the lights being current-responsive so as to increase in brightness if electrical power supplied to the lights increases, and the actuating means including means for supplying increasing current to at least one of the lights as a function of increasing velocity of the detected internal body matter.

5. In the device defined in claim 3, the probe having a hollow casing including a translucent portion and the lights being mounted inside said casing adjacent to said translucent portion for viewing through it.

6. In a medical Doppler device for detecting internal body matter and having a control unit and a hand-held transducer probe operably connected to but remote from such unit, the improvement comprising the combination of a visual indicator located on the probe, the probe having opposite sides, said indicator including at least tow electrically actuated lights of a first color and at least two electrically actuated lights of a second color different from the first color, said lights of the first color being mounted at opposite sides of the probe and said lights of the second color being mounted at opposite sides of the probe closely adjacent to said lights of the first color, respectively, and means for actuating said indicator to indicate whether the detected internal body matter is moving toward or away from the probe.

7. In a medical Doppler device for detecting internal body matter and having a control unit and a hand-held transducer probe operably connected to but remote from such unit, the improvement comprising the combination of a visual indicator located on the probe, the probe including an elongated hollow casing and a hollow tip portion having a closed end and an open end, said tip portion being mounted on said casing with the interior of said tip portion in communication with the interior of said casing, a flat circuit board fitted inside said tip portion and extending into said casing, at least one Doppler transducer mounted on said circuit board and received in said tip portion, said casing having a translucent portion overlying the circuit board, said indicator including at least one electrically actuated light contained within the tip portion adjacent to the translucent portion for viewing therethrough, and means for actuating said indicator to indicate whether the detected internal body matter is moving toward or away from the probe.

8. In the device defined in claim 7, the at least one light being mounted on the circuit board.

9. In the device defined in claim 7, the circuit board having opposite side edge portions and opposite faces extending between said side edge portions, the indicator including two electrically actuated lights of a first color mounted adjacent to the opposite side edge portions on opposite side faces of the circuit board, respectively, and two electrically actuated lights of a different color mounted adjacent to said lights of the first color on its opposite side faces, respectively, the actuating means including means for supplying electrical power to the lights of the first color if movement of detected internal body matter is toward the probe and for supplying electrical power to the lights of the different color if movement of the detected internal body matter is away from the probe.

10. In the device defined in claim 9, the lights being current-responsive so as to increase in brightness if electrical power supplied to the lights increases, and the actuating means including means for supplying increasing current to at least one of the lights as a function of increasing current of the detected internal body matter.

* * * * *